(12) United States Patent  (10) Patent No.: US 8,257,378 B1
O'Connor  (45) Date of Patent: Sep. 4, 2012

(54) ULTRASONIC GUIDE WIRE FOR DISINTEGRATION AND DISPERSION OF ARTERIAL OCCLUSIONS OF THROMBI AND PLAQUE

(76) Inventor: Lawrence R. O'Connor, Glendale, CA (US)

( * ) Notice: Subject to any disclaimer, the term of this patent is extended or adjusted under 35 U.S.C. 154(b) by 371 days.

(21) Appl. No.: 12/220,729

(22) Filed: Jul. 28, 2008

(51) Int. Cl.
*A61B 17/3205* (2006.01)
(52) U.S. Cl. ........................................................ 606/169
(58) Field of Classification Search .................. 600/437, 600/439; 604/22, 96.01, 103.01, 509; 606/159, 606/169, 191, 192, 194
See application file for complete search history.

(56) References Cited

U.S. PATENT DOCUMENTS 5,125,137 A * 6/1992 Corl et al. ..................... 29/25.35
5,846,218 A * 12/1998 Brisken et al. .................. 604/22
2004/0249401 A1* 12/2004 Rabiner et al. ................ 606/159
* cited by examiner

*Primary Examiner* — Ryan Severson
(74) *Attorney, Agent, or Firm* — Patrick F. Bright

(57) ABSTRACT

An angioplasty device for insertion into an artery having undesired deposits includes a guide wire for insertion into the artery; an elongated flexible catheter for insertion into the artery over the guide wire, the catheter having a proximal end, a distal end, and one or more lumens extending longitudinally therethrough; an energizable ultrasonic transducer inside the distal end of the guide wire; an inflatable balloon overlying the catheter and the transducer such that when the transducer is energized, energy from the transducer is transmitted through the balloon to the deposits.

3 Claims, 1 Drawing Sheet

ULTRASONIC GUIDE WIRE FOR DISINTEGRATION AND DISPERSION OF ARTERIAL OCCLUSIONS OF THROMBI AND PLAQUE

BACKGROUND OF THE INVENTION

This invention comprises an ultrasonic guide wire for insertion into arteries to disintegrate clots (thrombi) which accumulate on disrupted cholesterol plaques. The device proposed introduces a new form of treatment for arterial occlusions and obstructions. This new therapy may be called dispersion or disintegration thrombectomy.

Over time, cholesterol plaque builds up in coronary arteries. Later in life, these build-ups are attacked by the body's own immune system. These build-ups also become susceptible to ulceration and disruption. The tissue layer, or endothelial cap, that covers the plaque is attacked by white cell enzymes. The consequent thinning of the cap makes it susceptible to tearing by shear forces, exposing oxidized cholesterol contained within the plaque to the bloodstream. The body's clotting mechanism interprets this exposure as a perforation of the artery and activates to seal "the hole". Clot builds up on the obstructed plaque. The clot may obstruct the vessel and produce a syndrome called unstable angina. The volume of clot may be so large that it occludes the vessel and produces acute myocardial infarction (heart attack). Collectively, these events are called the acute coronary syndromes.

Increasingly, acute coronary syndromes are treated with percutaneous intervention. Current methods comprise threading a guide wire through the arterial obstruction or occlusion, and then sliding a balloon angioplasty catheter to the site of plaque disruption and clot formation. The balloon is inflated, fragmenting and dispelling the clot. Alternatively, a coronary stent may be deployed to reopen the artery, and trap the clot in its mesh structure. Unfortunately, with both of these methods, clot fragments are carried downstream and lodge in the capillaries of the heart muscle. This produces necrosis (patches of dead heart muscle) and reduces the function of the main pumping chamber called the left ventricle. The scarring, which results, may become the source of fatal heart rhythms. Worse yet, sludging of the fragments in the capillary bed may reduce blood flow, and result in a dangerous fall in blood pressure, or even patient death. None of the devices and methods proposed or developed to address these problems has been universally successful.

Some existing devices endeavor to capture clots downstream. These devices typically contain a deployable basket on a guide wire, but the baskets do not always expand completely within the downstream vessel. As a result, some clot slips around the edges of the basket.

Catheters designed to aspirate the thrombus do reduce the volume of a clot, but the impact is limited as demonstrated in recent scientific studies. Some clot remains attached to the plaque.

Consequently, there is a need for a device or apparatus which can remove up to 100% of the clot and mitigate fragment embolization downstream into the capillary bed of the heart muscle.

SUMMARY OF THE INVENTION

The devices of this invention disintegrate arterial clots into their constituent parts, e.g., microparticles and red blood cells. These cells and microparticles then flow through the capillary bed without sludging and without obstructing flow. The average red blood cell is 8µ in diameter and the average capillary through which it travels 20µ.

These devices comprise a piezo crystal embedded in a guide wire about one to about 20 cm from the distal tip. The guide wire can be used in conjunction with existing balloon catheters and stent delivery systems. The guide wire is advanced through a coronary artery to the site of a clot. Once the plaque in the clot has been passed with the guide wire, a balloon angioplasty catheter is advanced over the guide wire to the clot site, and the balloon is inflated. By positioning the piezo crystal on the body of the guide wire, low-power ultrasound energy can be delivered to the plaque/clot with precision. The guide wire is advanced or pulled back until the piezo crystal is in the middle of the inflated balloon. Power is delivered to the piezo crystal for a time period sufficient to disintegrate the clot. The inflated balloon acts as a sonic coupling device and focuses the ultrasound energy on the plaque/clot. The balloon is then deflated slowly and the microparticles allowed to flow downstream. These methods reduce large clot fragments to microparticles. Following clot disintegration, a coronary stent may be deployed to compress the remaining plaque and re-appose the disrupted layers. Cleaning the clot site reduces the chance of new clot buildup within the stent (acute stent thrombosis).

BRIEF DESCRIPTION OF THE DRAWINGS

This invention may be more clearly understood with the following detailed description and by reference to the drawings in which.

DETAILED DESCRIPTION OF THE PREFERRED EMBODIMENTS

Figure 1:
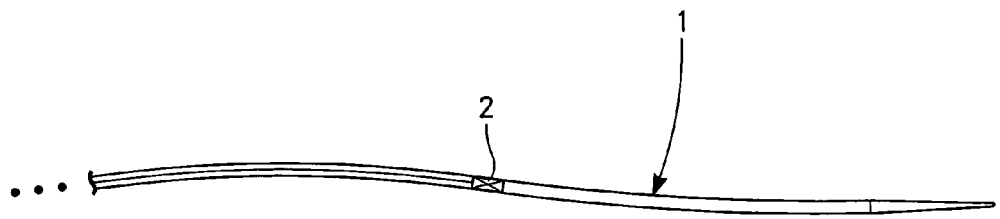
FIG. 1 is a perspective view of a guide wire with a piezo ultrasound device inside the guide wire.

FIG. 1 shows guide wire 1 with piezo crystal 2 placed inside guide wire 1. When activated, piezo crystal 2 delivers ultrasonic energy to anything in contact with crystal 2.

Figure 2:
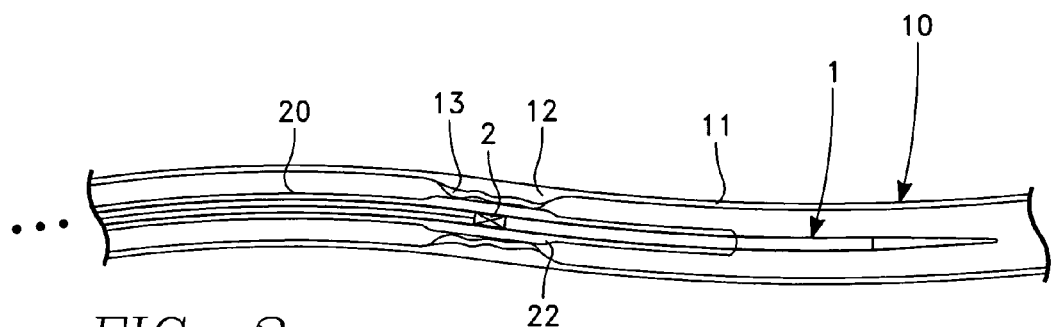
FIG. 2 is a perspective, cross-sectional view of the artery with the guide wire of FIG. 1 placed in an artery that has an internal disrupted plaque site with an adherent blood clot on the plaque, and with an uninflated balloon catheter deployed over the guide wire.

FIG. 2 shows a portion of the length of an artery 10 such as a coronary artery. The lumen 11 of artery 10 is partially occluded by artherosclertic plaque 12 embedded in the wall of artery 10. Because of the presence of calcified plaque 12, a crack or ulceration has occurred in the artery wall, resulting in a blood clot or thrombus 13 which has substantially blocked blood flow through artery 10. Inserted through thrombus 13 is guide wire 1 and a catheter 20 carrying a balloon 22. Balloon 22, when inflated as shown in FIG. 3, significantly opens the occluded part of the artery by pressing thrombus 13 against the internal wall of artery 10.

Balloon 22 traps thrombus 13, and couples/focuses ultrasonic energy from piezo crystal 2 into thrombus 13. Inside guide wire 1 is an ultrasonic transducer 2 (typically a piezoelectric member) connected to an ultrasonic signal source (not shown) adjacent the proximal end of guide wire 1.

Figure 3:
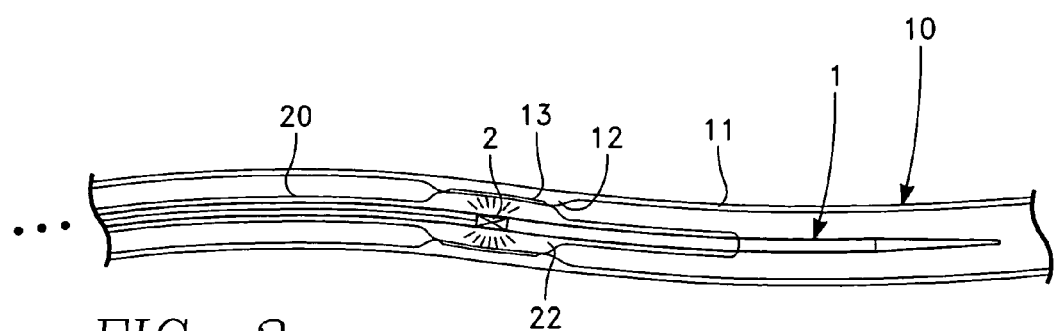
FIG. 3 is a perspective, cross-sectional view of the artery, a guide wire and balloon of FIG. 2 with the balloon inflated.

With the catheter 20, balloon 22 and transducer 2 positioned within artery 10 as shown, the balloon 22 is inflated through injection of a contrast agent as an aid in viewing the process as shown in FIG. 3. Balloon 22 presses against or traps thrombus 13 against the inner layer of artery 10. Balloon 22 is inflated to a pressure sufficient to cause full balloon expansion, adequate compression of thrombus clot and plaque, and trapping of these materials. Following inflation of balloon 22, the ultrasonic transducer 2 is energized, causing ultrasonic energy to pass through guide wire 1 and inflated balloon 22 to thrombus 13 and plaque 12. The aqueous solution in the balloon 22 readily transmits and focuses energy to the thrombus which breaks up the thrombus and plaque remnants into microparticulate matter with particles as small as 8 to 10 microns. These particles can then flow through the patient's cardiovascular system with minimal adverse effects.

The ultrasonic energy from transducer 2 may also create microfractures within the calcified plaque 12 which is embedded in the wall of artery 10. This leaves plaque 12 softer and susceptible to treatment by methods such as mechanical ablation or intracoronary stent.

The above-described embodiments of the present invention are merely descriptive, and are not to be considered limiting. The scope of this invention instead shall be determined from the scope of the following claims and equivalents.

What is claimed is:

1. An angioplasty device for insertion into an artery having undesired deposits comprising:
   a guide wire having a distal tip for insertion into said artery;
   an elongated flexible catheter for insertion into said artery over said guide wire, said catheter having a proximal end, a distal end, and at least one lumen extending longitudinally therethrough;
   an energizable ultrasonic transducer inside said guide wire about one to about 20 cm from said distal tip; and
   an inflatable balloon overlying said catheter and said transducer such that when said transducer is energized, energy from said transducer is transmitted through said balloon to said deposits.

2. A method of treating an undesired deposit in a blood vessel through the use of a guide wire having a distal tip, a catheter on the guide wire having a proximal end and a distal end, an ultrasonic transducer inside of said guide wire about one to about 20 cm from said distal tip, and an inflatable balloon on said catheter surrounding said ultrasonic transducer, the steps of:
   a) inserting said guide wire and catheter into said blood vessel until said balloon is adjacent to said deposit;
   b) inflating said balloon with suitable fluid to cause the outside surface of said balloon to come into contact with said deposit;
   c) energizing said ultrasonic transducer to provide ultrasonic energy flowing through said fluid to impact on said deposit and cause ablation of said deposit; and
   d) withdrawing said catheter, guide wire, balloon, and ultrasonic transducer from said blood vessel.

3. The method as claimed in claim 2 further comprising placing a stent coaxially on said catheter, and following step c), inflating said balloon to install said stent in the wall of said blood vessel.

* * * * *